(12) United States Patent
Lehoux et al.

(10) Patent No.: US 6,451,841 B2
(45) Date of Patent: Sep. 17, 2002

(54) METHOD OF DIFFUSING AN ACARICIDAL COMPOSITION COMPRISING PERMETHRIN AND TETRAMETHRIN, AND THE USE OF A CATALYTIC COMBUSTION FLASK FOR IMPLEMENTING SUCH A METHOD

(75) Inventors: Jannick Lehoux, Thuit Signol; Corinne Gomez, Louviers, both of (FR)

(73) Assignee: Produits Berger (FR)

( * ) Notice: Subject to any disclaimer, the term of this patent is extended or adjusted under 35 U.S.C. 154(b) by 0 days.

(21) Appl. No.: 09/760,168

(22) Filed: Jan. 12, 2001

(30) Foreign Application Priority Data

Jul. 6, 2000 (FR) .............................. 00 08824

(51) Int. Cl.$^7$ .............................................. A61K 31/40
(52) U.S. Cl. ........................................................ 514/421
(58) Field of Search ........................................ 514/421

(56) References Cited

U.S. PATENT DOCUMENTS

| | | | |
|---|---|---|---|
| 3,899,586 A | | 8/1975 | Okuno et al. |
| 4,292,322 A | * | 9/1981 | Muramoto et al. ......... 424/274 |
| 4,663,315 A | | 5/1987 | Hasegawa et al. |
| 4,968,487 A | | 11/1990 | Yamamoto et al. |
| 5,843,981 A | | 12/1998 | Miller |

FOREIGN PATENT DOCUMENTS

| | | |
|---|---|---|
| EP | 0064803 | 11/1982 |
| EP | 0120968 | 10/1984 |
| EP | 0639331 | 2/1995 |
| FR | 2599220 | 12/1987 |
| GB | 1447193 | 8/1976 |
| HU | T034100 | 2/1985 |
| HU | T042260 | 7/1987 |
| JP | 60142906 | 7/1985 |
| JP | 61151101 | 7/1986 |
| JP | 4117303 | 4/1992 |
| JP | 04120002 | 4/1992 |
| JP | 5229909 | 9/1993 |
| RU | 2139657 | * 4/1998 |
| RU | 2139657 | 10/1999 |
| WO | WO 97/47198 | 12/1997 |
| WO | WO 99/63267 | 12/1999 |

OTHER PUBLICATIONS

"Studies on the Insecticidal Effect of Vaporized Pyrethroid on Cockroaches", by Shinoda et al., Applied Ent. Zool. 18(4), pp. 517–524 (1983).

* cited by examiner

*Primary Examiner*—Alton N Pryor
(74) *Attorney, Agent, or Firm*—Bachman & LaPointe, P.C.

(57) ABSTRACT

The invention relates to a method of combating insects and parasites, and in particular acarids, the method comprising a step of diffusing a composition that includes permethrin in a solvent. The method is such that a composition is diffused in a chamber to be treated, the composition comprising permethrin and tetramethrin in a solvent, and it is diffused in such a manner that the solvent is entirely in the gaseous state.

17 Claims, 1 Drawing Sheet

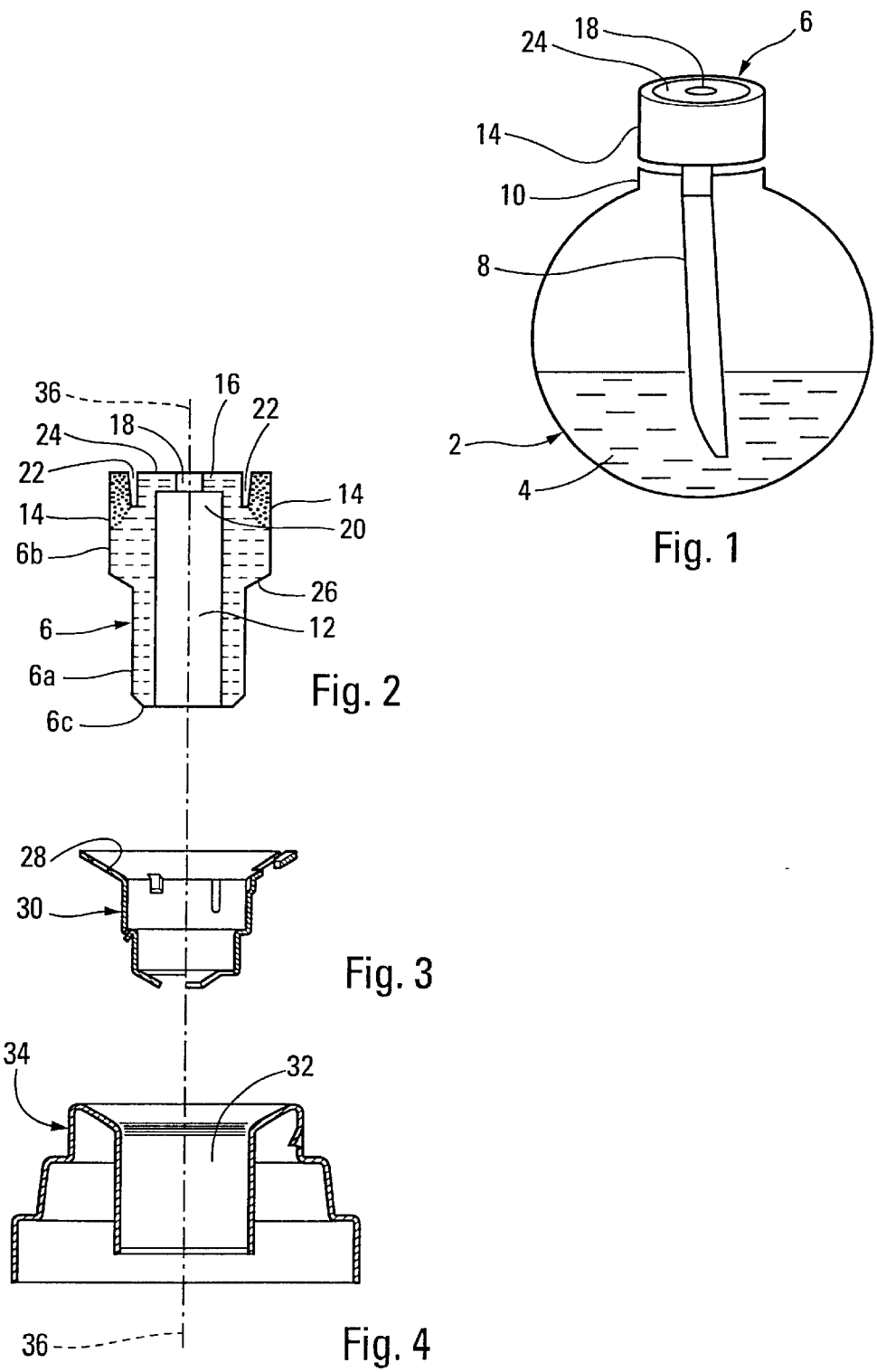

METHOD OF DIFFUSING AN ACARICIDAL COMPOSITION COMPRISING PERMETHRIN AND TETRAMETHRIN, AND THE USE OF A CATALYTIC COMBUSTION FLASK FOR IMPLEMENTING SUCH A METHOD

BACKGROUND OF THE INVENTION

The present invention relates to a method of combating certain pathogenic agents in the environment, such as insects and parasites, and in particular certain living creatures that give rise to allergies, specifically acarids or "mites".

The prior art which is described more specifically below is intended for combating acarids, but it should be understood that this description is in general transposable to most methods of combating most insects and parasites in the environment.

Products derived from pyrethrum such as pyrethrinoids are known to constitute substances that are highly toxic for cold-blooded creatures, such as insects and parasites, whereas they are less toxic for man and other warm-blooded creatures.

Compositions are known comprising a compound of the pyrethrinoid family in a solvent, with the pyrethrinoid commonly used being permethrin whose formula is $C_{21}H_{20}Cl_2O_3$; these compositions are generally activated (also said to be "synergized") by means of an activator (or "synergizer") such as piperonyl butoxide (PBO).

At present, numerous methods are used for combating acarids.

Thus, carpet cleaning shampoos and/or anti-acarid paints are used containing said compositions.

Studies have shown that when shampoos are applied, even with careful brushing, only some of the acarids are destroyed. Furthermore, those methods do not enable an entire room to be treated.

In addition to those treatments and in order to improve the destruction of acarids in a room, it is possible to diffuse compositions based on permethrin and PBO by means of a spray or an aerosol.

Although it is possible to use a spray or an aerosol to apply local treatment on surfaces soiled by acarids, under no circumstances is it possible for them to constitute means that are effective in eradicating all of the acarids present in a room.

Even under the optimistic assumption that a user has sprayed present compositions exhaustively over all surfaces, there nevertheless remains a non-negligible fraction of acarids that are not on the surface but that are inside certain items such as mattresses, carpets, . . . ; those acarids which cannot be destroyed by the above-described contact treatment operations will be able to develop and proliferate again.

At present, the most suitable treatment for combating acarids present in a residential room, both on its surfaces and within certain items such as mattresses, carpets, etc. . . . is to use a single-discharge aerosol.

That type of aerosol is calibrated as a function of the volume of the room to be treated and is designed to lower the population of acarids as much as possible in a single treatment.

Nevertheless, it suffers from the major drawback of being for a single use only. After being opened, such cans diffuse their composition that is active against acarids, i.e. an acaricidal composition, until they are completely empty.

Thus, in order to achieve effective treatment for a home, for example, it is necessary to purchase as many single-discharge aerosols as there are rooms in the home, and even then there remains the question of treating the common portions.

Such single-discharge aerosols also present the major drawback of preventing access to the room under treatment for several hours after the treatment operations have terminated because of the aggressive and irritant or even toxic nature of the active substance present in the concentrations that are obtained in the atmosphere of such a room.

Furthermore, all of the methods described above for using acaricidal compositions require compositions to be used whose concentration in permethrin, an active substance that is relatively expensive, lies in the range 1% to 3% by weight.

Furthermore, it is common practice to activate permethrin by using three times its weight of PBO, thereby increasing the cost of manufacturing such compositions, and thus the cost of the associated diffusion devices.

In addition, known methods are methods that act by the active substances in the liquid state coming into direct contact, either immediately when applying a shampoo or else after a greater or lesser delay when using a spray or an aerosol, and regardless of whether or not it is a single-discharge spray or aerosol. Those methods release either droplets of a size more or less fine that falls quickly onto surfaces, or else they release a mist constituted by finer droplets which remain longer in suspension, but nevertheless fall onto exposed surfaces within not more than a few hours.

OBJECTS AND SUMMARY OF THE INVENTION

The present invention seeks to mitigate all of the above-mentioned drawbacks and proposes a method of combating insects and parasites, and in particular acarids, the method comprising a step of diffusing an acaricidal composition comprising permethrin in a solvent.

According to the invention, the method is such that a composition comprising permethrin and tetramethrin in a solvent is diffused in a chamber to be treated, in such a manner that such solvent is entirely in the gaseous state.

Thus, the molecules with acaricidal action are distributed uniformly throughout the volume to be treated and they act on all zones that might contain colonies of acarids, penetrating into the smallest nooks and crannies.

The method is both simple to use and not very constraining. In particular, the user can come and go in the room and make free use of its furniture, even simultaneously with treatment operations taking place.

Furthermore, the acaricidal composition associated with the method of diffusion is genuinely effective by enabling volumes and their content to be thoroughly treated by acaricidal compositions having a concentration by weight of active substances well below the concentrations of present compositions.

This effectiveness applies not only to curative treatment of volumes, i.e. destroying colonies of acarids that are already prior art, but also to preventative treatment of such volumes, serving both to limit normal development of acarids up to the reproductive adult stage and to destroy any acarids that may be reintroduced into the treated volume from the outside (external recontamination).

The present invention thus presents the two advantages of using little active substance and of diffusing an acaricidal composition that presents no danger for the health of the user, by a surprising synergistic effect between the acaricidal composition and the method of diffusing it.

The saving achieved because of the small quantities of active substance used is further improved by the method acting relatively quickly.

In an advantageous version of the invention, about 0.05% to 0.5% (by weight) of permethrin is used together with about 0.05% to 0.5% (by weight) of tetramethrin.

In an advantageous version, about 0.1% to 0.4% (by weight) of permethrin is used together with about 0.1% to 0.4% (by weight) of tetramethrin.

In a preferred version, substantially equal proportions of permethrin and of tetramethrin are used, preferably both equal to about 0.2% (by weight).

The quantities of the pyrethrinoids are well below those commonly used with known diffusion methods.

The method of the invention gives rise to far fewer secondary effects for the user and presents a toxic effect that is well below that of known methods.

In a preferred implementation of the invention, the total proportion of permethrin plus tetramethrin used is about 0.15% to 0.8% (by weight), and preferably about 0.2% to 0.6% (by weight).

The total quantity of pyrethrinoids used in the context of the present invention is well below that of the prior art, and genuine effectiveness can be achieved at concentrations by weight that are reduced to one-fifth.

Advantageously, said composition is diffused by means of a catalytic combustion burner, the solvent being the fuel, and being constituted by isopropyl alcohol, for example.

The invention also provides the use of a catalytic combustion flask for implementing the method of the invention for combating insects and parasites, and in particular acarids, the flask being suitable for containing a combustible composition and to receive, on a collar fixed to its neck, a catalytic combustion burner, said burner having a substantially axial cavity that is downwardly open and that receives a wick dipping into said composition, said burner optionally having a substantially axial annular groove extending from the top surface of the burner and separating the annular peripheral zone carrying the catalyst from the central zone that is catalyst-free and forms a vaporization zone, the cavity being formed in a mass of ceramic material that is free from catalyst, and/or a channel for putting the top portion of the cavity that receives the wick into communication with the atmosphere.

BRIEF DESCRIPTION OF THE DRAWINGS

Other advantages and features of the invention appear from the following description given of non-limiting examples and made with reference to the accompanying figures, in which:

FIG. 1 is a diagrammatic elevation view of a flask fitted with a catalytic combustion burner that can be used for implementing the method of the present invention;

FIG. 2 is a diagrammatic axial section view on a larger scale of the burner shown in FIG. 1, in a preferred implementation of the method of the present invention;

FIG. 3 is a view similar to FIG. 2 showing an embodiment of a support for the FIG. 2 burner; and FIG. 4 is a view similar to FIG. 2 showing an embodiment of a collar suitable for receiving the FIG. 3 support.

DETAILED DESCRIPTION OF THE PREFERRED EMBODIMENTS

FIG. 1 shows a catalytic combustion flask 2 of the kind used for performing the tests which are described below.

The catalytic combustion flask 2 is adapted to contain a combustible composition 4 and to receive a catalytic combustion burner 6 at its top end which in turn receives a wick 8 that plunges into said composition 4.

The flask 2 can be of arbitrary shape providing it presents a neck 10 to which the burner 6 is fitted.

The combustible composition 4 comprises permethrin in a solvent.

As a general rule, the solvent belongs to the alcohol family, and is isopropyl alcohol, for example, but it could also comprise any other suitable liquid fuel compatible with the regulations in force. The liquid fuel should preferably be such that no disagreeable odor is given off when it vaporizes and when it is subjected to catalytic combustion.

The diffusion operation is performed by vaporizing the solvent when hot.

The combustible composition 4 of the invention may optionally also include a fragrance.

The wick 8 can be any known wick, e.g. a cotton wick. The wick could also be made of inorganic material, e.g. a mineral fiber wick.

As shown in detail in FIG. 2, the catalytic combustion burner 6 is a burner made of porous ceramic material, e.g. based on kaolin.

In its bottom portion 6a, the burner 6 has a substantially axial cavity 12 for receiving a wick 8 that is to feed the combustible composition 4 to the burner 6. The cavity 12 opens out at the bottom end 6c of the burner 6 and extends axially over the major portion of the axial size of the burner 6.

The top portion 6b of the burner 6 has an annular peripheral zone 14 supporting a catalyst, e.g. based on a metal belonging to group VIII of the periodic table for classifying elements. The annular peripheral zone 14 surrounds a catalyst-free central zone 16 that forms a vaporizing zone.

In the example shown in FIG. 2, the burner 6 has at least one open channel 18 in its top portion 6b putting the top portion 20 of the cavity 12 into communication with the atmosphere.

In this example and in conventional manner, the burner 6 has a substantially axial annular groove 22 extending downwards from the top surface 24 of the burner 6 on a diameter that is greater than the diameter of the cavity 12.

In conventional manner, this annular groove 22 provides a clear separation between the annular peripheral zone 14 supporting the catalyst and the central zone 16 of the top portion 6b.

The burner 6 has a peripheral shoulder 26 received by a complementary shoulder 28 of a support 30 as shown in FIG. 3.

The support 30 can be inserted directly into the neck 10 of the flask 2.

Usually, the support 30 is inserted into the central hole 32 of a collar 34 as shown diagrammatically in FIG. 4, and it is the collar 34 that is adapted to be fixed to the neck 10 of the flask 2.

The main effect of the support 30 is to urge the user of the burner 6 to put the support 30 and the burner 6 properly into place on the collar 34 on the common axis 36 of the neck 10, the collar 34, the support 30, and the burner 6.

There is nothing to prevent using other flask structures associated with a catalytic burner; in particular, the various flasks described in international patent application PCT/FR 99/00937 can advantageously be implemented in the context of the present invention.

The test chamber used in the context of the present experiments complies with present standards for testing insecticidal aerosols (AFNOR 72-320/BSI 4173/CEB 135bis), namely:

- a room in the form of a rectangular parallelepiped having a volume of 30 cubic meters ($m^3$), leakproof with walls that are smooth, washable, and inert relative to the substances to be tested (glass and inert white paint of the polyurethane resin type);
- a floor constituted by materials that are inert relative to the substances to be tested: white tiles.

The following devices were placed in the chamber:

- fluorescent tube lighting of the daylight type giving about 1500 lux at 50 cm from the light source and distributed uniformly throughout the room;
- optional dynamic ventilation provided by a fan for drying and renewing the air; the ventilation was total and automatic and provided by an extractor fan operating at a rate of 1200 cubic meters per hour ($m^3/h$); it was not active during testing; and
- regulated heating and humidification enabling given temperature and relative humidity to be maintained throughout testing.

During testing, conditions were as follows: 25° C. ±1° C., 70% ±5% relative humidity, and lighting at 1500 lux.

The chamber was fitted to represent as closely as possible a residential type room, and contained:

- three 15 cm wide shelves at three different heights (20 cm, 100 cm, and 150 cm from the floor);
- a board (0.5 m x 1 m) on legs representing a low table at a height of 80 cm; and
- an expanded polystyrene plate held vertically in a corner of the room and representing the location of a cupboard, for example (1 m wide, 15 cm gaps at the sides, 20 cm from the ground, 15 cm from the ceiling).

In the tests described and commented on below, three compositions were tested in succession:

composition I: tetramethrin +PBO composition II: permethrin +tetramethrin composition III: permethrin +tetramethrin +PBO.

Each composition to be tested was put into a flask of the type shown in FIG. 1 and fitted with a catalytic combustion burner as described with reference to FIG. 2.

After catalytic combustion had been initiated, the flask was moved into the room and placed in the center thereof at a height of 90 cm above the floor.

The composition under test was diffused by catalytic combustion for a period of about 30 minutes, after which diffusion was interrupted.

Two types of protocol were then carried out, firstly for evaluating the curative effects and secondly for evaluating the preventative or residual effects of each of the compositions.

In order to measure the curative effect of each composition, 100 acarids were put into the chamber after the 30 minutes of diffusing the composition under test. Thereafter, the number of dead acarids was measured at regular intervals, so as to determine the associated mortality rate.

To measure the preventative or residual effect, an area of carpet was put into the chamber at the end of the 30 minutes of the composition under test being diffused, and was therefore subjected to the same treatment as for evaluating curative effect. The carpet was taken out from the chamber 8 days after diffusion of the composition under test by catalytic combustion had been stopped. The area of carpet was inserted into the chamber after it had been infested with a determined number of new acarids and the mortality thereof was observed at regular 24-hour intervals.

The tests were performed on *Dermatophagoides pteronyssinus* acarids supplied by the Foodstuff Insect and Acarid Laboratory at the *Institute National de la Recherche Agronomique* (*INRA*) at Bordeaux.

For each of the compositions under test, treatment was repeated three times.

Furthermore, in parallel with each of the tests, control batches were subjected to the same handling.

The results of the tests are given below, for each of the compositions tested:

Composition I

Composition I was made by associating 0.4% by weight of tetramethrin with 1.16% by weight of piperonyl butoxide (PBO), the remainder being isopropyl alcohol.

The results obtained were as follows:

|  | Curative effect | | | | Residual or preventative effect | | | | Control | | | |
| --- | --- | --- | --- | --- | --- | --- | --- | --- | --- | --- | --- | --- |
| Test No. | 1 | 2 | 3 | Average | 1 | 2 | 3 | Average | 1 | 2 | 3 | Average |
| 24 h | 3 | 0 | 2 | 1.7 | 2 | 2 | 1 | 1.6 | 0 | 2 | 1 | 1.0 |
| 48 h | 11 | 16 | 12 | 13.0 | 3 | 4 | 3 | 3.3 | 3 | 5 | 4 | 4.0 |
| 72 h | 42 | 54 | 51 | 49.0 | 7 | 8 | 5 | 6.7 | 6 | 9 | 7 | 7.3 |
| 6 days | 79 | 91 | 87 | 85.7 | 12 | 15 | 10 | 12.3 | 11 | 16 | 11 | 12.7 |

Composition II

Composition II was made by associating identical quantities of tetramethrin and permethrin, i.e. 0.2% by weight of each of them, with the remainder being isopropyl alcohol.

The results obtained were as follows:

|  | Curative effect | | | | Residual or preventative effect | | | | Control | | | |
| --- | --- | --- | --- | --- | --- | --- | --- | --- | --- | --- | --- | --- |
| Test No. | 1 | 2 | 3 | Average | 1 | 2 | 3 | Average | 1 | 2 | 3 | Average |
| 24 h | 0 | 2 | 1 | 1.0 | 0 | 0 | 0 | 0.0 | 1 | 2 | 0 | 1.0 |
| 48 h | 27 | 22 | 31 | 26.7 | 8 | 9 | 13 | 10.0 | 2 | 3 | 2 | 2.3 |
| 72 h | 100 | 100 | 100 | 100.0 | 100 | 100 | 100 | 100.0 | 6 | 6 | 7 | 6.3 |

Composition III

Composition III was made by associating 0.4% by weight of tetramethrin, 0.2% by weight of permethrin, and 1.16% by weight of an activator, specifically piperonyl butoxide (PBO), the remainder being isopropyl alcohol.

The results obtained were as follows:

|  | Curative effect | | | | Residual or preventative effect | | | | Control | | | |
| --- | --- | --- | --- | --- | --- | --- | --- | --- | --- | --- | --- | --- |
| Test No. | 1 | 2 | 3 | Average | 1 | 2 | 3 | Average | 1 | 2 | 3 | Average |
| 24 h | 1 | 0 | 1 | 0.7 | 2 | 0 | 0 | 0.7 | 0 | 2 | 1 | 1.0 |
| 48 h | 25 | 30 | 27 | 27.3 | 11 | 7 | 9 | 9.0 | 1 | 3 | 3 | 2.3 |
| 72 h | 100 | 100 | 100 | 100.0 | 100 | 100 | 100 | 100.0 | 5 | 7 | 5 | 5.7 |

The numerical data demonstrates the proportion of dead acarids observed for each of the tests numbered 1 to 3, respectively after 24 h, 48 h, and then 72 h, and in one case after 6 days, this being measured:

to measure the curative effect, at the end of the composition in question being diffused for a period of 30 minutes; and to measure the residual or preventative effect, after a period of 8 days had elapsed since the composition in question had stopped being diffused.

In all of the tests performed, the control batches and also so-called "inter-test" tests (performed to verify that the chamber was not subject to external recontamination) presented mortality rates that were low or non-existent. Furthermore, the numerical data is very uniform from one test to another. Consequently the tests suffice for interpreting the results.

Tetramethrin, a compound whose formula is $C_{19}H_{25}O_4$ belongs like permethrin to the pyrethrinoid family and is known as an agent for striking down most flying or crawling insects.

The results obtained with composition I which associates tetramethrin with piperonyl butoxide are mediocre: the resulting curative effect was only 49% 3 days after the composition had ceased to be diffused, and only 86% at the end of 6 days. The mortality rate did not reach 100% after the composition had ceased to be diffused. The residual or preventative effect was also mediocre.

It can thus be seen that although synergized, tetramethrin does not appear to be a particularly effective substance for combating acarids.

However, surprisingly, it has been found that tetramethrin, when associated with permethrin and PBO, gives excellent results, both in curative and in preventative treatment.

The tests performed with composition II show that the method of the invention for diffusing such a composition by catalytic combustion is remarkably effective since 3 days after each of the compositions had been diffused, the experimental data shows that all of the acarids put into the chamber after said diffusion had been destroyed, even those that were put in 8 days after said diffusion.

Furthermore, the results turn out to be particularly surprising when comparing the data obtained with each of compositions II and III.

Composition II which firstly does not have a PBO type synergizer (a chemical which is nevertheless in very widespread use for activating permethrin), and in which the quantity of tetramethrin was halved compared with the quantity of tetramethrin used in composition III, nevertheless gave excellent results.

In the above-mentioned chamber having a volume of 30 m$^3$, a 100% curative effect was achieved in less than 72 hours; the preventative or residual effect was observed for a period of 8 days, and the total quantity of permethrin and tetramethrin diffused lay in the range 40 milligrams (mg) to 70 mg.

It can thus be considered that diffusing a total quantity lying in the range 1.33 milligrams per cubic meter (mg/m$^3$) to 2.33 mg/m$^3$ of permethrin and tetramethrin provides treatment that is effective for 8 days.

More generally, to treat a chamber effectively for 8 days, the total quantity of permethrin and tetramethrin diffused lies in the range 0.5 mg/m$^3$ to 3 mg/m$^3$, advantageously in the range 1 mg/m$^3$ to 2.5 mg/m$^3$, and preferably in the range 1.5 mg/m$^3$ to 2 mg/m$^3$.

The results obtained when diffusing composition II also show that there is no need to add a PBO type synergizer in that type of acaricidal composition, which thus constitutes a very significant industrial advantage.

On the contrary, the results show that real synergy exists between permethrin and tetramethrin.

It can thus be seen that using catalytic combustion to diffuse compositions associating specifically permethrin and tetramethrin at very low concentrations by weight, well below the compositions commonly used to combat acarids, achieves diffusion that is fine and optimum for said compositions, serving not only to apply curative treatment to volumes, but also to provide treatment that is remanent over time, as measured by the residual or preventative effect.

Acarids are also considered as presenting much greater resistance than insects, particularly flies.

The method of the invention is thus also recommended for destroying flies and other insects or parasites.

It is believed that this surprising result is due to the fact that the composition associating permethrin and tetramethrin is diffused in particularly fine manner.

Naturally, the present invention is not limited to the embodiments described above and numerous changes or modifications can be made thereto without going beyond the ambit of the invention.

What is claimed is:

1. A method of combating insects and parasites comprising the steps of:

providing a composition comprising permethrin and tetramethrin in a combustible solvent;

diffusing said composition in a chamber to be treated; and said diffusing step being performed using a catalytic combustion burner made of porous ceramic material and comprising a top portion including a top end and a bottom portion including a bottom end, said bottom portion comprising a substantially axial cavity for receiving a wick dipping into said composition for feeding said composition to said burner, said cavity being opened out at said bottom end of said burner, being extended axially over the major portion of the axial size of said burner and being separated by a wall from said top end of said burner, and said top portion having an annular peripheral zone supporting a catalyst, said annular peripheral zone surrounding a catalyst-free central zone that forms a vaporizing zone.

2. A method according to claim 1, wherein said permethrin is used at a concentration in the range of about 0.05% to 0.5% by weight and said tetramethrin is used at a concentration in the range of about 0.05% to 0.5% by weight.

3. A method according to claim 2, wherein said permethrin is used at a concentration in the range of about 0.1% to 0.4% by weight.

4. A method according to claim 2, wherein said tetramethrin is used at a concentration in the range of about 0.1% to 0.4% by weight.

5. A method according to claim 1, wherein identical concentrations of said permethrin and said tetramethrin are used in said composition.

6. A method according to claim 1, wherein said permethrin and said tetramethrin are both present in said composition at a concentration of about 0.2% by weight.

7. A method according to claim 1, wherein said permethrin and said tetramethrin are present in said composition at a total concentration in the range of about 0.15% to 0.8% by weight.

8. A method according to claim 7, wherein said total concentration of permethrin and tetramethrin is in the range of about 0.2% to 0.6% by weight.

9. A method according to claim 1, wherein for effective treatment of said chamber during a period of eight days, said diffusing step comprises diffusing a total quantity of said permethrin plus said tetramethrin in the range of from 0.5 $mg/m^3$ to 3 $mg/m^3$ into said chamber.

10. A method according to claim 9, wherein said diffusing step comprises diffusing a total quantity of permethrin plus tetramethrin in the range of 1.0 $mg/m^3$ to 2.5 $mg/m^3$.

11. A method according to claim 9, wherein said diffusing step comprises diffusing a total quantity of said permethrin plus said tetramethrin in the range of 1.5 $mg/m^3$ to 2.0 $mg/m^3$.

12. A method according to claim 1, wherein said composition providing step comprises adding an activator to said composition.

13. A method according to claim 12, wherein said activator adding step comprises adding piperonyl butoxide to said composition.

14. A method according to claim 1, wherein said combustible solvent is isopropyl alcohol.

15. A method according to claim 1, further including a step of operating a system comprising:

a flask containing said composition;

said flask having a neck and a collar fixed to said neck; and said catalytic combustion burner received by said collar.

16. A method according to claim 15, wherein said system operating step further comprises providing said burner with a substantially axial annular groove extending from a top surface of the burner and said groove separating an annular peripheral zone carrying a catalyst from a central zone that is catalyst-free and that forms a vaporization zone.

17. A method according to claim 16, wherein said burner providing step comprises providing said burner with a channel for putting a top portion of the cavity into communication with the atmosphere and said wick being received in said top portion of the cavity.

* * * * *